(12) United States Patent
Ahlgren

(10) Patent No.: US 12,091,817 B2
(45) Date of Patent: Sep. 17, 2024

(54) REACTOR DISCHARGE SCREW

(71) Applicant: VALMET AB, Sundsvall (SE)

(72) Inventor: Örjan Ahlgren, Sundsvall (SE)

(73) Assignee: VALMET AB, Sundsvall (SE)

( * ) Notice: Subject to any disclaimer, the term of this patent is extended or adjusted under 35 U.S.C. 154(b) by 630 days.

(21) Appl. No.: 17/289,001

(22) PCT Filed: Oct. 30, 2019

(86) PCT No.: PCT/SE2019/051080
§ 371 (c)(1),
(2) Date: Apr. 27, 2021

(87) PCT Pub. No.: WO2020/091675
PCT Pub. Date: May 7, 2020

(65) Prior Publication Data
US 2021/0404116 A1 Dec. 30, 2021

(30) Foreign Application Priority Data

Oct. 31, 2018 (SE) .................................... 1851352-3

(51) Int. Cl.
*D21C 7/08* (2006.01)
*B01J 19/20* (2006.01)
(Continued)

(52) U.S. Cl.
CPC .............. *D21C 7/08* (2013.01); *B65G 33/14* (2013.01); *B65G 53/48* (2013.01); *B65G 65/46* (2013.01); *D21C 1/02* (2013.01); *B01J 19/20* (2013.01)

(58) Field of Classification Search
CPC .......... D21C 7/08; B65G 65/46; B65G 53/48; B65G 33/14; B65G 33/26
See application file for complete search history.

(56) References Cited

U.S. PATENT DOCUMENTS 3,519,532 A * 7/1970 Sutherland ............... D21C 7/08
162/272
3,540,604 A * 11/1970 Hyttinen ............ B65G 65/4827
222/410

(Continued)

FOREIGN PATENT DOCUMENTS

WO WO 97/39177 A1 10/1997

*Primary Examiner* — Jacob T Minskey
*Assistant Examiner* — Matthew M Eslami
(74) *Attorney, Agent, or Firm* — Foley & Lardner LLP

(57) ABSTRACT

The invention relates to a discharge screw arrangement (12) for discharging lignocellulosic material (7) from a lignocellulosic treatment reactor (1) and comprises a discharge screw (10), a feeder pipe (11) and a blow pipe (5), the discharge screw being accommodated in and rotatably arranged inside the feeder pipe and being configured to mechanically transport the lignocellulosic material in a longitudinal direction along a rotational axis of the discharge screw through the feeder pipe towards a downstream end (14) of the feeder pipe, which discharge screw arrangement is configured to allow steam to flow through the feeder pipe to help transporting the lignocellulosic material in the longitudinal direction along through the feeder pipe and out of the feeder pipe through an outlet nozzle (24) arranged in a side wall of the feeder pipe (11) at the downstream end of the feeder pipe and into the blow pipe, wherein the discharge screw arrangement further comprises a material spreader (20), which is rotatably arranged at the downstream end of the feeder pipe and is configured to transport the lignocellulosic material in a radial direction, perpendicular to a rotational axis of the material spreader, towards the outlet nozzle, which is arranged peripherally of the material spreader, and out of the feeder pipe through the outlet nozzle and into the blow pipe.

11 Claims, 1 Drawing Sheet

(51) Int. Cl.
    *B65G 33/14*     (2006.01)
    *B65G 53/48*     (2006.01)
    *B65G 65/46*     (2006.01)
    *D21C 1/02*     (2006.01)

(56) References Cited

U.S. PATENT DOCUMENTS

| | | |
|---|---|---|
| 2004/0238133 A1 | 12/2004 | Lashofer et al. |
| 2006/0108083 A1 | 5/2006 | Gabl et al. |
| 2008/0277082 A1 | 11/2008 | Pschorn et al. |
| 2021/0237024 A1* | 8/2021 | Mellander ............... D21C 7/08 |

* cited by examiner

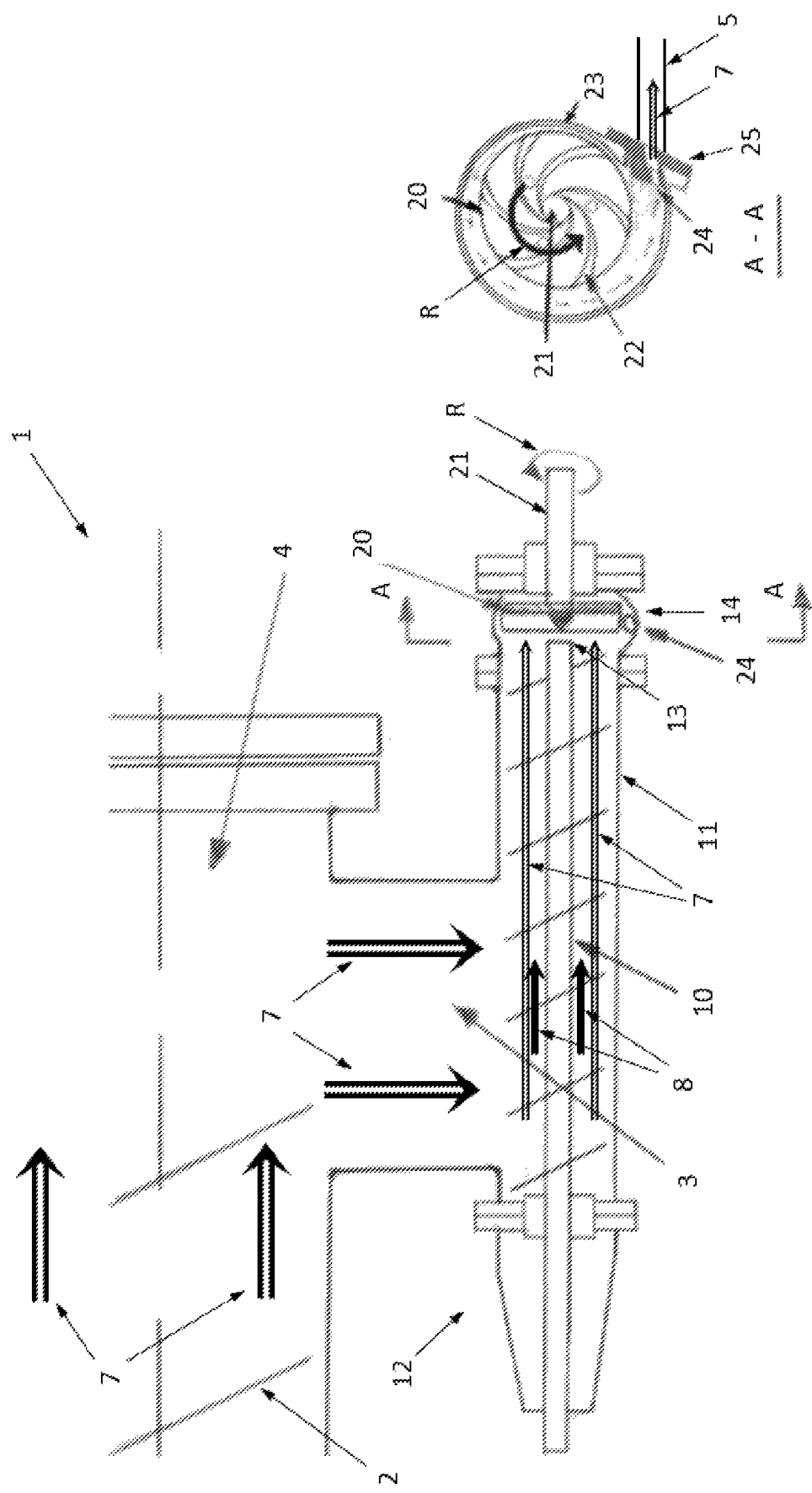

REACTOR DISCHARGE SCREW

TECHNICAL FIELD

The present invention generally relates to treatment of lignocellulosic material in a reactor, and more particularly to a discharge screw for discharging such material from the reactor.

BACKGROUND

The area of the present invention originates in refining of lignocellulosic material for the production of pulp for e.g. papermaking but has in recent years broadened to also include pre-treatment of lignocellulosic material for further processing resulting in biofuel, such as e.g. bioethanol. Lignocellulosic material or biomass is abundant and can provide a sustainable resource for producing e.g. fuels, chemicals and biobased materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network. The hemicelluloses removal is a key step of the pulp production process and is carried out in a steam or water pre-hydrolysis stage. Typically, a horizontal tube reactor is used for pre-hydrolysis of the lignocellulosic material. For higher biomass feed capacities vertical reactors become more cost effective.

The horizontal tube reactor or digester has been adapted to conditions applied in the pre-hydrolysis process. Pre-hydrolysis is sometimes called hydro-thermal treatment or just pre-treatment since it is a treatment step before enzymatic hydrolysis. Pre-hydrolysis is typically performed at acid conditions, high temperature and pressure up to 25 bar. The primary application for tube digesters has been processing of agricultural residues such as bagasse and wheat straw or other annual plants for the production of fibers for papermaking.

In a typical horizontal reactor, an internal conveyor screw transports/feeds the biomass material through the reactor, which gives the biomass a well-controlled retention time. Direct steam for heating is added along the reactor. Depending on the feed rate and retention time, several tube reactors can be connected in series.

The discharge or blowing of material from the reactor can be hot or cold depending on the requirements in subsequent steps. With hot blow steam explosion takes place which means disintegration of the biomass into small particles. This may be beneficial e.g. in a subsequent saccharification step since the enzymes used in such a step are given excellent access to the material.

Cold blow, or dilution discharge, is applied when the objective is to separate the sugars dissolved in the liquid phase during the pre-hydrolysis from the remaining solid biomass. It gives the possibility to treat the sugars dissolved in the pre-hydrolysis, mainly from hemicelluloses, separately. Separation of the liquid from the biomass is done in fiber washing equipment.

After treatment in the reactor, the lignocellulosic material is discharged from the reactor for further transport to subsequent processing equipment. In prior art reactors, a large amount of steam is needed in order to discharge the often wet and heavy material from the reactor. This results in a high steam consumption in the reactor. From experience we know that about 1-2 tons of steam for every tonne of raw material is required to feed the material from the reactor and out into a subsequent blow pipe. It is anticipated that a more effective outfeed from the reactor could reduce the steam consumption in the reactor.

Therefore, there is a need for a more effective discharge/blowing of lignocellulosic material out from the reactor.

SUMMARY

It is an object to provide a discharge screw which improves the discharge/blowing of lignocellulosic material out from a lignocellulosic treatment reactor, thereby lowering the steam consumption in the reactor.

This and other objects are met by embodiments of the proposed technology.

According to a first aspect of the invention a discharge screw arrangement for discharging lignocellulosic material from a lignocellulosic treatment reactor is provided, which discharge screw arrangement comprises a discharge screw, a feeder pipe and a blow pipe, the discharge screw being accommodated in and rotatably arranged inside the feeder pipe, where the discharge screw is configured to mechanically transport the lignocellulosic material in a longitudinal direction along a rotational axis of the discharge screw through the feeder pipe towards a downstream, with respect to a material transport direction, end of the feeder pipe, and where the discharge screw arrangement is configured to allow steam flowing through the feeder pipe to help transporting the lignocellulosic material in the longitudinal direction along the rotational axis of the discharge screw through the feeder pipe towards the downstream end of the feeder pipe, out of the feeder pipe through an outlet nozzle arranged in a side wall of the feeder pipe at the downstream end of the feeder pipe and into the blow pipe which is located adjacent to the outlet nozzle on the outside of the feeder pipe, wherein the discharge screw arrangement further comprises a material spreader rotatably arranged at the downstream end of the feeder pipe, where the material spreader is configured to transport the lignocellulosic material in a radial direction, perpendicular to a rotational axis of the material spreader, towards the outlet nozzle which is arranged peripherally of the material spreader, out of the feeder pipe through the outlet nozzle and into the blow pipe.

According to one embodiment of the invention, the discharge screw arrangement further comprises an upstream surface of the material spreader which is provided with vanes for improving the transport of lignocellulosic material towards the outlet nozzle.

The discharge screw arrangement can further comprise at least one motor which is configured to rotate the material spreader and the discharge screw, wherein the at least one motor is configured to rotate the material spreader at a rotational speed which is faster than a rotational speed of the discharge screw. The at least one motor can further be configured to rotate the material spreader at a rotational speed which is equal to a rotational speed of the discharge screw.

According to a second aspect, there is provided a lignocellulosic treatment reactor comprising a discharge screw arrangement as defined above.

An advantage of the proposed technology is that a lower amount of steam is needed to discharge/blow the lignocellulosic material out from the reactor, which means that the steam consumption in the reactor will be significantly lower.

Other advantages will be appreciated when reading the detailed description.

BRIEF DESCRIPTION OF THE DRAWINGS

The invention, together with further objects and advantages thereof, can best be understood by making reference to the following description taken together with the accompanying drawings, in which:

FIG. 1 is a schematic illustration of a part of a reactor for treatment of lignocellulosic material and a discharge screw arrangement for discharging lignocellulosic material from the reactor according to an embodiment of the present disclosure.

DETAILED DESCRIPTION

The present invention generally relates to treatment of lignocellulosic material in a reactor, and more particularly to a discharge screw for discharging such material from the reactor.

Throughout the drawings, the same reference designations are used for similar or corresponding elements.

As described in the background section there is continued need in the art to improve the discharge/blowing of lignocellulosic material out from a lignocellulosic treatment reactor in order to lower the steam consumption in the reactor.

As described above, in a typical horizontal reactor, an internal conveyor screw transports/feeds the lignocellulosic material/biomass through the reactor. At the end of the internal conveyor screw in the reactor the material falls down vertically through a reactor discharge unit into a second, smaller conveyor screw or discharge screw which runs at a higher speed and transports the material towards an outlet nozzle, which is typically located at the end of the discharge screw. The material is transported from the last part of the discharge screw into and through the nozzle and out into a blow pipe outside of the discharge screw by means of steam at high velocity. The steam velocity must be very high to be able to transport this often wet and heavy material from the end of the screw towards and out through the outlet nozzle. If a sudden increase in material flow occurs, there is a possibility that the steam does not provide enough force to transport the material through the nozzle with a risk that the nozzle may get plugged. Therefore, a high amount of steam is needed to transport the material from the last part of the discharge screw into the nozzle. From experience we know that about 1-2 tons of steam for every tonne of raw material is required to feed the material from the end of the screw into the outlet nozzle. With the present invention which provides a more effective outfeed from the reactor, it is anticipated that only about 0.3-0.5 tons of steam for every tonne of fiber should be required.

According to the present disclosure, an improved discharge/blowing of lignocellulosic material out from a lignocellulosic treatment reactor can be accomplished by introducing a reactor discharge screw arrangement which feeds the lignocellulosic material forwards towards a rotating material spreader arranged at the downstream end of the discharge screw arrangement, where the rotating material spreader throws/transports the material out to the periphery of the discharge screw arrangement where the outlet nozzle is located. With this design a lower amount of steam is needed in order to transport the lignocellulosic material out through the outlet nozzle, since mechanical transport is utilized instead of, or in combination with, steam flow for transporting the often wet and heavy material from the center of the discharge screw arrangement towards the periphery of the discharge screw arrangement where the outlet nozzle is located.

FIG. 1 is a schematic illustration of a part of a reactor 1 for treatment of lignocellulosic material 7 with a discharge screw arrangement 12 for discharging the lignocellulosic material 7 from the reactor 1 according to an embodiment of the present disclosure. As illustrated in the figure, a rotating internal conveyor screw 2 located inside a reactor vessel 4 in the reactor 1 transports the lignocellulosic material 7 through the reactor vessel 4 towards a downstream, with respect to the material transport direction, end of the reactor vessel 4, where the lignocellulosic material 7 enters into the discharge screw arrangement 12.

The discharge screw arrangement 12 comprises a rotating discharge screw 10 accommodated in and rotating inside a feeder pipe/screw pipe 11. The rotations of the internal conveyor screw 2 and the discharge screw 10 are driven by motors (not shown in the figure). In a particular embodiment the discharge screw arrangement 12 is located vertically below the reactor vessel 4 at the downstream end of the reactor vessel 4, and the lignocellulosic material 7 falls down vertically from the reactor vessel 4 into the discharge screw 10, possibly via a reactor discharge unit 3 located between the reactor vessel 4 and the discharge screw 10 at the downstream end of the reactor vessel 4.

The lignocellulosic material 7 is mechanically transported by the discharge screw 10 in a longitudinal direction, i.e. along the rotational axis of the discharge screw 10, through the feeder pipe 11 towards a downstream, with respect to the material transport direction, end 14 of the feeder pipe 11, where a material spreader 20, e.g. in the form of a rotating disc in an embodiment, is arranged. The centripetal force due to the rotation of the material spreader 20 throws the lignocellulosic material 7 in a radial direction, i.e. perpendicular to the rotational axis of the rotating material spreader 20, towards the periphery of the material spreader 20 and the periphery of the discharge screw arrangement 12, and towards an outlet nozzle 24 arranged at the periphery of the discharge screw arrangement 12, i.e. peripherally of the material spreader 20 at the downstream end 14 of the feeder pipe 11. Thereby, the lignocellulosic material 7 is discharged by the material spreader 20 out of the feeder pipe 11 through the outlet nozzle 24 and into a discharge pipe/blow pipe 5 located adjacent to the outlet nozzle 24 on the outside of the feeder pipe 11. This is illustrated in the right part of FIG. 1 which shows a cross-section along the line A-A of the left part of FIG. 1. The outlet nozzle 24 can in an embodiment be arranged e.g. in a side wall of the feeder pipe 11. In a particular embodiment, the outlet nozzle 24 and the blow pipe 5 are located basically vertically below the material spreader 20.

As also illustrated in FIG. 1, steam 8 flowing through the feeder pipe 11 also helps transporting the lignocellulosic material 7 through the feeder pipe 11 towards the downstream end 14 of the feeder pipe 11 and out through the outlet nozzle 24. In a particular embodiment, the steam 8 transports the material 7 from the downstream end 13 of the discharge screw 10 towards the downstream end 14 of the feeder pipe 11. With the currently disclosed embodiments, a lower amount of steam is needed than in prior art discharge screw arrangements, since the material spreader in the present embodiments utilizes mechanical transport for transporting the material from the center of the discharge screw arrangement towards the periphery of the discharge screw arrangement where the outlet nozzle is located.

The upstream surface of the material spreader 20, i.e. the surface facing the incoming material flow from the discharge screw 10, can in an embodiment be provided with wings or vanes 22 for improving the material transport towards the outlet nozzle 24. The rotating material spreader 20 can in an embodiment rotate on a shaft 21 inside e.g. a housing 23 in a rotational direction R, as illustrated in FIG. 1. The rotational speed of the material spreader 20 can be faster than the rotational speed of the discharge screw 10 in an embodiment, or it can be the same as the rotational speed of the discharge screw 10 in another embodiment. In a particular embodiment, the material spreader 20 can be a part of, or integrated with, the discharge screw 10.

The outlet nozzle 24 can have an opening of adjustable size in an embodiment. A discharge valve 25 arranged adjacent to the outlet nozzle 24 can be utilized to adjust the discharge of the material from the feeder pipe 11 into the blow pipe 5.

In a particular embodiment the reactor 1 is a horizontal reactor.

Another possible utilization of the material spreader is to perform mechanical work on the raw lignocellulosic material, such as to remove carbon lumps or decrease the size of the raw material. If used in such an application, the material spreader can be equipped with a bigger motor and/or rotor/rotating disc.

With the present embodiments a lower amount of steam is needed to discharge/blow the lignocellulosic material out from the reactor, which means that the steam consumption in the reactor will be significantly lower.

The embodiments described above are merely given as examples, and it should be understood that the proposed technology is not limited thereto. It will be understood by those skilled in the art that various modifications, combinations and changes can be made to the embodiments without departing from the present scope as defined by the appended claims. In particular, different part solutions in the different embodiments can be combined in other configurations, where technically possible.

The invention claimed is:

1. A discharge screw arrangement for discharging lignocellulosic material from a lignocellulosic treatment reactor, the discharge screw arrangement comprising:
   a feeder pipe comprising a side wall, wherein an outlet nozzle is located in the side wall at a downstream end of the feeder pipe with respect to a material transport direction;
   a blow pipe located outside the feeder pipe and communicating with outlet nozzle;
   a discharge screw rotatably arranged inside the feeder pipe, the discharge screw configured to:
      mechanically transport the lignocellulosic material in the longitudinal direction along the rotational axis of the discharge screw, through the feeder pipe, and toward the downstream end of the feeder pipe, and
      allow steam to flow through the feeder pipe in a longitudinal direction along a rotational axis of the discharge screw towards the downstream end of the feeder pipe, out of the feeder pipe through the outlet nozzle, and into the blow pipe; and
   a material spreader rotatably arranged at the downstream end of the feeder pipe along the rotational axis of the discharge screw, the material spreader is configured to transport the lignocellulosic material in a radial direction perpendicular to a rotational axis of the material spreader, towards the outlet nozzle, which is arranged peripherally of the material spreader, out of the feeder pipe through the outlet nozzle, and into the blow pipe.

2. The discharge screw arrangement according to claim 1, wherein an upstream surface of the material spreader comprises vanes configured to facilitate transport of the lignocellulosic material towards the outlet nozzle.

3. The discharge screw arrangement according to claim 1, further comprising at least one motor configured to rotate the material spreader and the discharge screw, wherein the at least one motor is configured to rotate the material spreader at a rotational speed which is faster than a rotational speed of the discharge screw.

4. The discharge screw arrangement according to claim 1, further comprising at least one motor configured to rotate the material spreader and the discharge screw, wherein the at least one motor is configured to rotate the material spreader at a rotational speed which is equal to a rotational speed of the discharge screw.

5. The discharge screw arrangement according to claim 4, wherein the material spreader is a part of the discharge screw.

6. The discharge screw arrangement according to claim 1, wherein the outlet nozzle has an opening of adjustable size.

7. The discharge screw arrangement according to claim 1, further comprising a discharge valve arranged adjacent to the outlet nozzle and configured to adjust discharge of lignocellulosic material from the feeder pipe into the blow pipe.

8. The discharge screw arrangement according to claim 1, wherein the discharge screw arrangement is adapted for a horizontal reactor.

9. A lignocellulosic treatment reactor comprising:
   the discharge screw arrangement according to claim 1; and
   a reactor vessel configured to provide the lignocellulosic material to the discharge screw arrangement.

10. The lignocellulosic treatment reactor according to claim 9, further comprising:
   an internal conveyor screw located inside the reactor vessel and configured to transport the lignocellulosic material through the reactor vessel towards a downstream end of the reactor vessel with respect to the material transport direction; wherein:
   the discharge screw arrangement is configured to receive the lignocellulosic material from the reactor vessel at the downstream end of the reactor vessel.

11. The lignocellulosic treatment reactor according to claim 10, wherein:
   the reactor is a horizontal reactor; and
   the discharge screw arrangement is located vertically below the reactor vessel at the downstream end of the reactor vessel, such that the lignocellulosic material can fall vertically from the reactor vessel into the discharge screw arrangement at the downstream end of the reactor vessel.

* * * * *